United States Patent [19]

Uneme et al.

[11] Patent Number: 5,084,459
[45] Date of Patent: Jan. 28, 1992

[54] TETRAHYDROPYRIMIDINES, THEIR PRODUCTION AND USE

[75] Inventors: Hideki Uneme, Osaka; Isao Minamida, Kawabe; Tetsuo Okauchi, Hirakata; Noriko Higuchi, Matsubara, all of Japan

[73] Assignee: Takeda Chemical Industries, Ltd., Osaka, Japan

[21] Appl. No.: 426,177

[22] Filed: Oct. 25, 1989

[30] Foreign Application Priority Data

Oct. 26, 1988 [JP] Japan .................................. 63-270064
Jul. 17, 1989 [JP] Japan .................................. 1-184312

[51] Int. Cl.⁵ .................. C07D 401/04; C07D 403/04; C07D 413/12; C07D 417/12; A01N 43/54; A01N 43/66; A01N 43/713; A01N 239/47; A01N 239/42; A01N 401/12; A01N 401/14
[52] U.S. Cl. .................................. 514/269; 514/256; 514/252; 514/241; 514/245; 514/248; 514/231.5; 514/228.8; 514/227.8; 514/266; 514/249; 514/250; 514/225.5; 514/225.8; 514/226.8; 514/227.2; 514/229.8; 544/236; 544/383; 544/257; 544/295; 544/296; 544/238; 544/298; 544/326; 544/328; 544/329; 544/322; 544/327; 544/180; 544/192; 544/198; 544/212; 544/209; 544/207; 544/220; 544/216; 544/217; 544/218; 544/219; 544/221; 544/222; 544/223; 544/264; 544/265; 544/122; 544/123; 544/98; 544/56; 544/58.1; 544/58.2; 544/58.4; 544/58.5; 544/53; 544/54; 544/55; 544/60; 544/68; 544/237; 544/35; 544/102; 544/235

[58] Field of Search .................. 514/256, 225.5, 227.2, 514/252, 248, 227.8, 250, 225.8, 229.8, 241, 231.5, 266, 226.8, 269, 245, 228.8, 249; 544/326, 236, 295, 298, 322, 192, 209, 216, 219, 223, 122, 56, 58.5, 55, 237, 235, 283, 296, 328, 327, 198, 207, 217, 221, 264, 123, 58.1, 53, 60, 35, 257, 238, 329, 180, 212, 220, 218, 222, 265, 98, 58.4, 54, 68, 102

[56] References Cited

FOREIGN PATENT DOCUMENTS 0005984 12/1979 European Pat. Off. .
0247477 12/1987 European Pat. Off. .

OTHER PUBLICATIONS

Masakatsu SONE et al., "Reaction of 1-Nitro-2,2-bis(-methylthio), ethylene. V. Reaction with Amines, Faculty of Pharmaceutical Sciences", Nagasaki University, vol. 97 (1977) pp. 262-269 (with partial translation).

Primary Examiner—John M. Ford
Attorney, Agent, or Firm—Wegner, Cantor, Mueller & Player

[57] ABSTRACT

There is provided a pest control composition containing a compound represented by the formula,

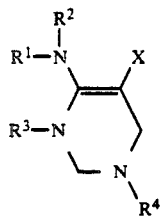

wherein $R^1$, $R^2$, $R^3$ and $R^4$ are the same or different and independently mean a hydrogen atom, a hydrocarbon group which may be substituted or a heterocyclic group which may be substituted and X means an electron attracting group or a salt thereof.

The compounds are of minimal toxicity to man, domestic animals and fish and selectively display remarkable control effect on pests.

17 Claims, No Drawings

TETRAHYDROPYRIMIDINES, THEIR PRODUCTION AND USE

BACKGROUND OF THE INVENTION

1. Field of the Invention

The present invention relates to tetrahydropyrimidine compounds and salts thereof, which are of use as pesticides, processes for production thereof, and pest control compositions containing said compounds or salts.

2. Brief Description of the Prior Art

While many synthetic compounds having pesticidal activity have heretofore been employed as pesticides, the majority of them belong to the categories of organic phosphates, carbamates, organochlorine compounds and pyrethroids. It is well known that the ubiquitous use of compounds of such limited varieties has resulted in serious outcomes such as the increased resistance of pests to pesticides everywhere in the world. Furthermore, some of the above-mentioned pesticides are highly toxic to man, domestic animals and aquatic life and even to the natural enemies of pests and cause so serious a soil residue problem that they are not considered to be very useful.

OBJECTS AND SUMMARY OF THE INVENTION

It is a primary object of the invention to provide novel pesticidal compounds which are of minimal toxicity man, domestic animals and fish and selectively display remarkable control effects on pests.

It is another object to provide processes for producing said pesticidal compounds.

It is a further object to provide a pesticidal composition useful for selective control of pests.

Other objects and advantages of the present invention will become apparent from a perusal of this specification.

The inventors of the present invention conducted intensive and diligent research for developing an insecticidal compound having an entirely novel structure and found surprisingly that a tetrahydropyrimidine compound of the formula

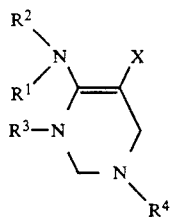

[I]

wherein $R^1$, $R^2$, $R^3$ and $R^4$ are the same or different and independently represent a hydrogen atom, a hydrocarbon group which may be substituted or a heterocyclic group which may be substituted and X represents an electron attracting group, as well as a salt thereof, has very potent pesticidal activity and very low toxicity. The present invention was conceived on the basis of the above finding. The present invention is therefore directed to:

(1) a pest control composition containing the above tetrahydropyrimidine compound [I] or a salt thereof;

(2) a novel tetrahydropyrimidine compound subsumed in the category of said compound [I] and having the formula

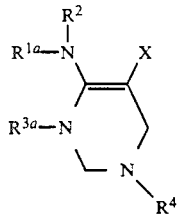

[I$^a$]

wherein $R^{1a}$, $R^2$, $R^{3a}$ and $R^4$ are the same or different and independently mean a hydrogen atom, a hydrocarbon group which may be substituted or a heterocyclic group which may be substituted; at least one of $R^{1a}$ and $R^{3a}$ is a group of the formula $-(CH_2)_n-R^5$ (where $R^5$ is a heterocyclic group which may be substituted or a substituted hydrocarbon group; and n means 0 or 1); and X has the same meaning as defined hereinbefore or a salt thereof;

(3) a tetrahydropyrimidine compound or salt (2) wherein $R^5$ is a halopyridyl group or a halothiazolyl group;

(4) a pesticidal composition (1) wherein the tetrahydropyrimidine compound or salt is the compound (2) or (3); and (5) a process for producing a tetrahydropyrimidine compound [I$^a$] or a salt thereof which comprises:
(i) reacting a compound of the formula

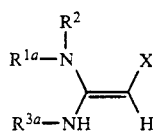

[II]

wherein all the symbols have the same meanings as defined hereinbefore or a salt thereof with an amine of the formula $R^4-NH_2$  [III]

wherein $R^4$ has the same meaning as defined hereinbefore or a salt thereof and formaldehyde;
(ii) reacting a compound of the formula

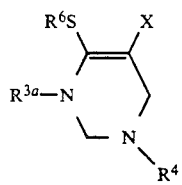

[IV]

wherein $R^{3a}$, $R^4$ and X have the same meanings as defined hereinbefore and $R^6$ means a lower alkyl group or a salt thereof with an amine of the formula

[V]

wherein $R^{1a}$ and $R^2$ have the same meanings as defined hereinbefore or a salt thereof; or (iii) reacting a compound of the formula

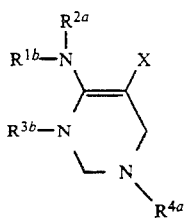

[VI]

where $R^{1b}$, $R^{2a}$, $R^{3b}$ and $R^{4a}$ are such that at least one of them means a hydrogen atom with the remainder independently meaning a hydrocarbon group which may be substituted or a heterocyclic group which may be substituted and X has the same meaning as defined hereinbefore or a salt thereof with a compound of the formula $$R^7-Y \quad [VII]$$

wherein $R^7$ means a hydrocarbon group which may be substituted or a heterocyclic group which may be substituted and Y means a halogen atom or an alkylsulfonyloxy, arylsulfonyloxy or acyloxy group which may be substituted by halogen.

Referring to the above formulas, the hydrocarbon group of said hydrocarbon group which may be substituted, i.e. $R^1$, $R^2$, $R^3$, $R^4$, $R^{1a}$, $R^{3a}$, $R^{1b}$, $R^{2a}$, $R^{3b}$, $R^{4a}$ or $R^7$, and the hydrocarbon group of said substituted hydrocarbon group, i.e. $R^5$, may include alkyl groups of 1 to 15 carbon atoms, such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl, pentadecyl, etc.; cycloalkyl groups of 3 to 10 carbon atoms, such as cyclopropyl, cyclobutyl, cyclopentyl, cyclohexyl, etc.; alkenyl groups of 2 to 10 carbon atoms, such as vinyl, allyl, 2-methylallyl, 2-butenyl, 3-butenyl, 3-octenyl, etc.; alkynyl groups of 2 to 10 carbon atoms, such as ethynyl, 2-propynyl, 3-hexynyl, etc.; cycloalkenyl groups of 3 to 10 carton atoms, such as cyclopropenyl, cyclopentenyl, cyclchexenyl, etc.; aryl groups of 6 to 10 carbon atoms, such as phenyl, naphthyl, etc.; and aralkyl groups of 7 to 10 carbon atoms, such as benzyl, phenylethyl and so on. The substituent or substituents on said hydrocarbon group which may be substituted and the substituent or substituents on said substituted hydrocarbon group include, among others, nitro, hydroxyl, oxo, thioxo, cyano, carbamoyl, carboxy, $C_{1-4}$ alkoxycarbonyl groups such as methoxycarbonyl, ethoxycarbonyl etc., sulfo, halogen atoms such as fluorine, chlorine, bromine, iodine, etc.; lower ($C_{1-4}$)alkoxy groups such as methoxy, ethoxy, propoxy, isopropoxy, butoxy, isobutoxy, s-butoxy, t-butoxy, etc., phenoxy and halophenoxy groups such as o-, m- or p-chlorophenoxy, o-, m- or p-bromophenoxy, etc., lower $C_{1-4}$ alkylthio groups such as methylthio, ethylthio, n-propylthic, isopropylthio, n-butylthio, t-butylthio, etc., phenylthio, $C_{1-4}$ alkylsulfinyl groups such as methylsulfinyl, ethylsulfinyl, etc., $C_{1-4}$ alkylsulfonyl groups such as methylsulfonyl, ethylsulfonyl, etc., amino, $C_{2-6}$ acylamino groups such as acetylamino, propionylamino, etc., such substituted amino groups as methylamino, ethylamino, n-propylamino, isopropylamino, n-butylamino, dimethylamino, diethylamino, cyclohexylamino, anilino, etc., $C_{2-4}$ acyl groups such as acetyl etc., benzoyl, five- or six-membered heterocyclic groups containing 1 to 4 hetero-atoms selected from the class consisting of oxygen, sulfur and nitrogen, such as 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isooxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl, indolyl, etc. (each of these heterocyclic groups may have 1 to 4 substituents such as halogen atoms, e.g. Br, Cl, F, etc., $C_{1-4}$ alkyl groups, e.g. methyl, ethyl, propyl, isopropyl, etc., and halophenoxy groups, e.g. o-, m- or p-chlorophenoxy, o-, m- or p-bromophenoxy, etc.), and halo $C_{1-10}$ alkyl groups such as difluoromethyl, trifluoromethyl, trifluoroethyl, trichloroethyl, etc. One to 5 such substituents as above may be present, and where the hydrocarbon group is an aryl, aralkyl, cycloalkyl or cycloalkenyl group, 1 to 5 of said alkyl, alkenyl, alkynyl and/or aryl groups may be present.

The heterocyclic group of said heterocyclic group which may be substituted, i.e. $R^1$, $R^2$, $R^3$, $R^4$, $R^{1a}$, $R^{3a}$, $R^{1b}$, $R^{2a}$, $R^{3b}$, $R^{4a}$, $R^5$ or $R^7$, may be a five- to eight-membered ring containing 1 to 5 hetero-atoms such as oxygen, sulfur and/or nitrogen, or a fused ring derived therefrom, such as 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazoly, 2-, 4- or 5-imidazolyl, 3-, 4- or 5-isooxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H or 2H-tetrazolyl, N-oxido-2,3- or 4-pyridyl, 2-, 4- or 5-pyrimidinyl, N-oxido-2,4- or 5-pyrimidinyl, 3- or 4-pyridazinyl, pyrazinyl, N-oxido-3- or 4-pyridazinyl, benzofuryl, benzothiazolyl, benzoxazolyl, triazinyl, oxotriazinyl, tetrazolo[1,5-b]pyridazinyl, triazolo[4,5-b]pyridazinyl, oxoimidazinyl, dioxotriazinyl, pyrrolidinyl, piperidinyl, pyranyl, thiopyranyl, 1,4-oxazinyl, morpholinyl, 1,4-thiazinyl, 1,3-thiazinyl, piperazinyl, benzimidazolyl, quinolyl, isoquinolyl, cinnolinyl, phthalazinyl, quinazolinyl, quinoxalinyl, indolidinyl, quinolidinyl, 1,8-naphthyridinyl, purinyl, pteridinyl, dibenzofuranyl, carbazolyl, acridinyl, phenanthridinyl, phenazinyl, phenothiazinyl, phenoxazinyl and so on. As to the substituents on said heterocyclic group which may be substituted, there may exist 1 to 5 substituents selected from among the substituent groups mentioned for said hydrocarbon group which may be substituted.

Preferred examples of $R^1$, $R^{1a}$ and $R^{1b}$ include a hydrogen atom, a $C_{1-4}$ alkyl group such as methyl, ethyl, propyl, isopropyl, butyl, etc., and groups of the formula $-(CH_2)_n-R^{5a}$ (where $R^{5a}$ means a five- or six-membered nitrogen-containing heterocyclic or $C_{6-10}$ aryl group which may be substituted by halogen; n has the same meaning as defined hereinbefore). As the common examples of said five- or six-membered nitrogen-containing heterocyclic group $R^5$, there may be mentioned pyridyl and thiazolyl, and the $C_{6-10}$ aryl group may for example be phenyl. These groups may be substituted by 1 to 3 halogen atoms such as chlorine and bromine. Preferred examples of $R^2$ and $R^{2a}$ include a hydrogen atom, a $C_{1-4}$ alkyl group such as methyl, ethyl, propyl, isopropyl, butyl, etc. and $C_{1-4}$ acyl groups such as formyl etc. Particularly desirable is a hydrogen atom. Preferred examples of $R^3$, $R^{3a}$ and $R^{3b}$ are those mentioned as preferred examples of $R^1$, $R^{1a}$ and $R^{1b}$ and it is preferable that they are different from the groups $R^1$, $R^{1a}$ and $R^{1b}$. Since $R^4$ and $R^{4a}$ have no significant influence on the pesticidal potency of compound [I], many examples may be cited for these groups Thus, for example, $C_{1-4}$ alkyl groups such as methyl, ethyl, propyl, isopropyl, butyl, t-butyl, etc., hydroxy $C_{1-4}$ alkyl groups such as hydroxymethyl, 2-hydroxyethyl, 2-hydroxypropyl, etc.; halo $C_{1-4}$ alkyl groups such as bromomethyl, chloroethyl, trifluoroethyl, etc.; $C_{3-6}$ cycloalkyl groups such as cyclopropyl, cyclopentyl, cyclohexyl, etc.; and groups of the formula $-(CH_2)_n-R^{5a}$ (wherein $R^{5a}$ and n have the same meanings as defined hereinbefore) may be mentioned.

As examples of $R^6$, there may be mentioned lower ($C_{1-4}$) alkyl groups such as methyl, ethyl, n-propyl, isopropyl, n-butyl, t-butyl and so on.

The symbol n represents 0 or 1.

The electron-attracting group X includes, among others, cyano, nitro, alkoxycarbonyl (such as $C_{1-4}$ alkoxycarbonyl groups, e.g. methoxycarbonyl, ethoxycarbonyl, etc.), hydroxycarbonyl, $C_{6-10}$ aryloxycarbonyl (e.g. phenoxycarbonyl), heterocycle-oxycarbonyl (the heterocycle of which may be any of those mentioned hereinbefore; e.g. pyridyloxycarbonyl, thienyloxycarbonyl, etc.), $C_{1-4}$ alkylsulfonyl which may be substituted by halogen (Cl, Br, etc.) (such as methylsulfonyl, trifluoromethylsulfonyl, ethylsulfonyl, etc.), sulfamoyl, di-$C_{1-4}$ alkoxyphosphoryl (e.g. diethoxyphosphoryl etc.), $C_{1-4}$ acyl group which may be substituted by halogen (Cl, Br, etc.) and/or the like (such as acetyl, trichloroacetyl, trifluoroacetyl, etc.), carbamoyl, $C_{1-4}$ alkylsulfonylthiocarbamoyl (such as methylsulfonylthiocarbamoyl etc.) and so on. The most preferred electron-attracting group is nitro, to name but one species.

The halogen atom Y may for example be chlorine, bromine, iodine or fluorine. The alkylsulfonyloxy group which may be substituted by halogen (Cl, Br, F, etc.) includes, among others, $C_{1-4}$ alkylsulfonyloxy groups, such as methanesulfonyloxy, ethanesulfonyloxy, butanesulfonyloxy, trifluoromethanesulfonyloxy, etc., which may be substituted by 1 to 3 halogen atoms. The arylsulfonyloxy group which may be substituted by halogen includes, among others, $C_{6-10}$ arylsulfonyloxy groups, such as benzenesulfonyloxy, p-toluenesulfonyloxy, p-bromobenzenesulfonyloxy, mesitylenesulfonyloxy, etc., which may be substituted by 1 to 4 halogen atoms (Cl, Br, F, etc.). The acyloxy group which may be substituted by halogen includes, among others, acetyloxy, propionyloxy, benzoyloxy and so on.

As preferred examples of tetrahydropyrimidine compound [I] or salt thereof, there may be mentioned the compounds which can be represented by the formula

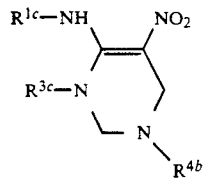
[$I^b$]

wherein $R^{1c}$ and $R^{3c}$ are such that one of them is a group of the formula $-CH_2-R^{5b}$ (wherein $R^{5b}$ means a halopyridyl or halothiazolyl group) with the other meaning a $C_{1-4}$ alkyl group; and means a $C_{1-4}$ alkyl group. In the above formula, the $C_{1-4}$ alkyl group designated by any of $R^{1c}$, $R^{3c}$ and $R^{4b}$ includes among others, methyl, ethyl, propyl, isopropyl, butyl, isobutyl, t-butyl and so on. $R^{5b}$ means, for example, a halopyridyl group such as 6-chloro-3-pyridyl, 6-bromo-3-pyridyl, 6-chloro-2-pyridyl, 5-bromo-3-pyridyl, etc. or a halothiazolyl group such as 2-chloro-5-thiazolyl, 2-bromo-5-thiazolyl, 2-chloro-4-thiazolyl and so on.

As salts of tetrahydropyrimidine compound [I], [$I^a$] or [$I^b$], there may be mentioned salts with inorganic acids such as hydrochloric acid, hydrobromic acid, hydroiodic acid, phosphoric acid, sulfuric acid, perchloric acid, etc. and salts with organic acids such as formic acid, acetic acid, tartaric acid, malic acid, citric acid, oxalic acid, succinic acid, benzoic acid, picric acid, p-toluenesulfonic acid and so on.

For use of tetrahydropyrimidine compound [I] or a salt thereof as a pesticide, one or more species of compound [I] or salt is dissolved or dispersed in a suitable liquid vehicle or admixed with, or adsorbed on, a suitable solid carrier to provide a preparation which is known in the art, such as an emulsifiable concentrate, oil, wettable powder, dust, granule, tablet, aerosol, ointment or the like. If necessary, any emulsifier, suspending agent, spreading agent, penetrating agent, wetting agent, thickner (muscilage etc.), stabilizer, etc. may be incorporated. These preparations can be manufactured by the per se known production processes.

While the proportion of the active compound in such a pesticidal composition varies with intended use, an appropriate range is about 10 to 90 percent by weight in the case of an emulsifiable concentrate or a wettable powder, about 0.1 to 10 percent by weight in the case of an oil or a dust, or about 1 to 20 percent by weight for granules. Deviations from these ranges are permissible depending on intended uses. The emulsifiable concentrate and wettable powder are diluted with water or the like (about 100 to 100,000-fold) and the dilutions are applied.

Suitable examples of the liquid vehicle (solvent) include water, alcohols (e.g. methanol, ethanol, n-propanol, isopropyl alcohol, ethylene glycol, etc.), ketones (e.g. acetone, methyl ethyl ketone, etc.), ethers (e.g. dioxane, tetrahydrofuran, ethylene glycol monomethyl ether, diethylene glycol monomethyl ether, propylene glycol monomethyl ether, etc.), aliphatic hydrocarbons (e.g. kerosene, fuel oil, machine oil, etc.), aromatic hydrocarbons (e.g. benzene, toluene, xylene, solvent naphtha, methylnaphthalene, etc.), halogenated hydrocarbons (e.g. methylene chloride, chloroform, carbon tetrachloride, etc.), acid amides (e.g. dimethylformamide, dimethylacetamide, etc.), esters (e.g. ethyl acetate, butyl acetate, fatty acid glycerol ester, etc.), nitriles (e.g. acetonitrile, propionitrile, etc.) and so on. These solvents may be used as a mixture prepared by mixing two or more of them in a suitable ratio.

Examples of said solid carrier (diluent/volume builder) include vegetable powders (e.g. soybean meal, tobacco flour, wheat flour, sawdust, etc.), mineral powders (such as clays, e.g. kaolin, bentonite, acid clay, etc., talcs, e.g. talcum powder, agalmatolite (pyrophyllite) powder, etc., and silicas such as diatomaceous earth, mica powder, etc.), alumina, sulfur powder, activated carbon and so on. These carriers may be used as a mixture prepared by mixing two or more of them in a suitable ratio.

Ointment bases which can be employed include polyethylene glycol, pectin, polyhydric alcohol esters of higher fatty acids such as monostearic acid glycerol ester etc., cellulose derivatives such as methylcellulose etc., sodium alginate, bentonite, higher alcohols, polyhydric alcohols such as glycerol etc., vaseline, white petrolatum, liquid paraffin, lard, vegetable oils, lanolin, dehydrated lanolin, hydrogenated oils, resins, etc. These bases can be used alone or in combination, or as supplemented with surfactants such as those mentioned hereinafter.

The surfactants which can be employed as said emulsifier, spreading agent, penetrating agent or dispersing agent include various soaps and nonionic or anionic surfactants such as polyoxyethylene alkyl aryl ethers [such as Noigen ® and E.A 142 ®, Dai-Ichi Kogyo Seiyaku Co.; Nonal ®, Toho Chemical Co.], alkyl sulfates [e.g. Emal 10 ® & Emarl 40 ®, Kao Corporation), alkyl sulfonates (e.g. Neogen ® & Neogen I ®, Dai-Ichi Kogyo Seiyaku Co.; Neopellex ®, Kao Corporation), polyethylene glycol ethers (Nonipol 85 ®, Nonipol 100 ® & Nonipol 160 ®, Sanyo Chemical Industries], polyhydric alcohol esters (e.g. Tween 20 ® & Tween 80 ®, Kao Corporation) and so on.

The tetrahydropyrimidine compound [I] and salt thereof can be used in combination with other kinds of insecticides (pyrethrin insecticides, organophosphorus insecticides, carbamate insecticides, natural insecticides, etc.), miticides, nematocides, herbicides, plant hormones, plant growth regulators, fungicides (for example, copper fungicides, organochlorine fungicides, organosulfur fungicides, phenolic fungicides, etc.), synergists, attractants, repellents, pigments, fertilizers, etc. in suitable ratios.

The tetrahydropyrimidine compound [I] and salt thereof are effective in controlling household pests and pests parasitizing plants or animals and exhibit potent pesticidal effects on pests which are directly exposed thereto. However, a more outstanding feature of the pesticide of the invention is that after the active chemical is absorbed into the plant from its root, leaf or stem, the pest sucking, gnawing or otherwise contacting the plant is exposed to the potent pesticidal action of the chemical. This characteristic is advantageous for the purpose of controlling sucking or gnawing pests. Furthermore, the compound [I] and its salt are least toxic to useful plants and fish, thus being possessed of the safe and useful property necessary for agrochemicals.

The agrochemical composition containing the tetrahydropyrimidine compound [I] or a salt thereof is particularly effective in the control of harmful insects of the order *Hemiptera* such as *Eurydema rugosum, Scotinophara lurida, Riptortus clavatus, Stephanitis nashi, Laodelphax striatellus, Nilaparvata lugens, Nephotettix cincticeps, Unaspis yanonensis, Aphis glycines, Lipaphis erysimi, Brevicoryne brassicae, Aphis gossypii*, etc., harmful insects of the order *Lepidoptera* such as *Spodoptera litura, Plutella xylostella, Pieris rapae crucivora, Chilo suppressalis, Autographa nigrisigna, Helicoverpa assulta, Pseudaletia separata, Mamestra brassicae, Adoxophyes orana fascia Notarcha derogata, Cnaphaloorocis medinalis, Phthorimaea operculella*, etc., harmful insects of the order *Coleoptera* such as *Epilachna viqintioctopunctata, Aulacophora femoralis, Phyllotreta striotata, Oulema oryzae, Echinocnemus squameus*, etc., harmful insects of the order *Diptera* such as *Musca domestica, Culex pipiens pallens, Tabanus trigonus, Delia antiqua, Delia platura*, etc., harmful insects of the order *Orthoptera* such as *Locusta migratoria, Gryllotalpa africana*, etc., harmful insects of the family *Blattoidae* such as *Blattella germanica, Periplaneta fuliginosa*, etc., pests of the order *Acarina* such as *Tetranychus urticae, Panonychus citri, Tetranychus kanzawai, Tetranychus cinnabarinus,* *Panonychus ulmi, Aculops pelekassi*, and nematodes such as *Aphelenchoides besseyi* and so on.

The pesticide provided by the present invention is very low in toxicity and is useful as an agrochemical. This pesticide can be used in the same manner as the conventional pesticide and, yet, provides effects surpassing those of the latter. For example, the pesticide of the invention can be used in the treatment of nursery pots or foliage of crop plants, direct application to pests, treatment of irrigation water for paddy fields or soil treatment. The application amount may be varied over a broad range according to the timing and site of application and the method of application. Generally speaking, the pesticide is used in an amount corresponding to about 0.3 to 3,000 g, preferably 50 to 1,000 g, as active ingredient (tetrahydropyrimidine compound [I] or salt thereof) per hectare. When the pesticide of the invention is supplied in the form of a wettable powder, it is applied as diluted to a final concentration of 0.1 to 1,000 ppm, preferably 10 to 500 ppm, as active compound.

The tetrahydropyrimidine compound [I$^a$] or salt thereof can be produced by any of the following processes (A) through (F). When the compound [I$^a$] made available by such processes is a free compound, it can be converted to a salt and when it is a salt, the salt can be converted to the free compound, by the per se known procedures, respectively.

When a species of compound [I$^a$] is used as a starting material for another species of compound [I$^a$], it can be used as it is, i.e. the free compound or the salt.

In the following description of the production processes, compounds [I$^a$], [II], [III], [IV], [V] and [VI], inclusive of salts thereof, are referred to briefly as compounds [I$^a$], [II], [III], [IV], [V] and [VI], respectively.

(A) Compound [I$^a$] is produced a by reacting compound [II] with compound [III] and formaldehyde While these compounds [II] and [III] can be used in the free form, they may be converted to salts like those described for compound [I] and used as such. Relative to compound [II], compound [III] is used preferably in a proportion of about 1.0 to 1.5 equivalents and formaldehyde in a proportion of about 2 to 4 equivalents. However, unless the reaction is adversely affected, compound [III] may be used in a proportion ranging from about 1.5 to 10 equivalents and formaldehyde in a proportion of about 4 to 20 equivalents. For the purposes of this reaction, formaldehyde is generally used in the form of aqueous solution (formalin) but may be paraformaldehyde or formaldehyde gas.

While the reaction may be carried out in the absence of a solvent, it is generally conducted in a solvent. The solvent includes, among others, water, alcohols such as methanol, ethanol, n-propanol, isopropyl alcohol, etc., aromatic hydrocarbons such as benzene, toluene, xylene, etc., halogenated hydrocarbons such as dichloromethane, chloroform, etc., saturated hydrocarbons such as hexane, heptane, cyclohexane, etc., ethers such as diethyl ether, tetrahydrofuran (THF), dioxane, etc., ketones such as acetone etc., nitriles such as acetonitrile etc., sulfoxides such as dimethyl sulfoxide (DMSO) etc., acid amides such as N,N-dimethylformamide (DMF), esters such as ethyl acetate etc., and carboxylic acids such as acetic acid, propionic acid and so on. These solvents may be used in admixture in an appropriate ratio of such as, 1:1 through 1:10. When the reaction mixture is not homogenous, the reaction may be conducted in the presence of a phase transfer catalyst such as quaternary ammonium salts including triethybenzylammonium chloride, tri-n-octylmethylammonium chloride, trimethyldecylammonium chloride, tetramethylammorium bromide, etc. and crown ethers.

This reaction can be conducted with advantage in the presence of an acid. The acid includes, among others, hydrohalogenic acids such as hydrochloric acid, hydrobromic acid, etc., phosphoric acid, and lower carboxylic acids such as acetic acid, propionic acid and so on. The acid is used in an amount ranging from a catalyst amount to a large excess.

This reaction generally proceeds at a temperature between 0° and 40° C. but may be hastened by heating the reaction system at a temperature from 40° C. to 100° C. The reaction time is generally 2 to 20 hours under no heating and about 10 minutes to 5 hours under heating.

(B) Compound [I$^a$] is produced by reacting compound [IV] with compound [V]

While the compounds [IV] and [V] can be used in the free form, they may be used in the form of salts like those mentioned for compound [I]. Relative to compound [IV], compound [V] is used preferably in a proportion of about 0.8 to 1.5 equivalents. However, unless the reaction is adversely affected, about 1.5 to 10 equivalents of [V] can be employed.

This reaction is conducted either in the absence of a solvent or in the presence of a solvent such as those mentioned for process (A). When the reaction system is not homogenous, a phase transfer catalyst such as those mentioned for process (A) can be employed.

This reaction may be conducted in the presence of a base or a metal salt for reducing the reaction time. The base mentioned just above includes, among others, various inorganic bases such as sodium hydrogen carbonate, potassium hydrogen carbonate, sodium carbonate, potassium carbonate, sodium hydroxide, potassium hydroxide, calcium hydroxide, phenyllithium, butyllithium, sodium hydride, potassium hydride, sodium methoxide, sodium ethoxide, sodium metal, potassium metal, etc. and various organic bases such as triethylamine, tributylamine, N,N-dimethylaniline, pyridine, lutidine, collidine, 4-dimethylaminopyridine, DBU (1,8-diazabicyclo[5,4,0]undecene-7) and so on. The abovementioned organic bases may be used as the solvent as well. As the above-mentioned metal salt, there may be used any of copper salts such as copper chloride, copper bromide, copper acetate, copper sulfate, etc. and mercury salts such as mercury chloride, mercury nitrate, mercury acetate and so on.

The reaction temperature may range from −20° C. to 150° C. and the reaction time from 10 minutes to 20 hours. The preferred temperature and time are 0° to 80° C. and 1 to 10 hours.

The tetrahydropyrimidine compound [I$^a$] can be produced also by reacting compound [VI] or a salt thereof with compound [VII]. This reaction is specifically described below under (C) through (F).

(C) When a compound of the formula [VI] wherein R$^{2a}$=H or a salt thereof is used as the starting material A compound of the formula

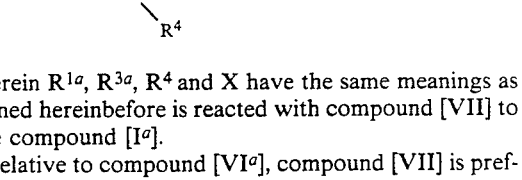

wherein R$^{1a}$, R$^{3a}$, R$^4$ and X have the same meanings as defined hereinbefore is reacted with compound [VII] to give compound [I$^a$].

Relative to compound [VI$^a$], compound [VII] is preferably used in a proportion of about 0.8 to 1.5 equivalents but, unless the reaction is adversely affected, can be used in large excess.

This reaction can be hastened by conducting it in the presence of a base, and the base for this purpose may be selected, for example, from those mentioned for process (B). Relative to compound [VI$^a$], the base can be used in a proportion ranging from about 0.5 equivalent to a large excess, preferably about 0.8 to 1.5 equivalents. When an organic base is used, it may serve as a solvent as well.

Generally speaking, this reaction is preferably conducted in a solvent such as those mentioned for process (A) and when the reaction system is not homogenous, a phase transfer catalyst such as those mentioned for process (A) can be employed. The reaction temperature is generally −20° to 150° C. and preferably 0° to 80° C. The reaction time is generally 10 minutes to 50 hours and preferably 2 to 20 hours.

(D) A compound of the formula [VI] wherein R$^{4a}$=H or a salt thereof is used as the starting material A compound of the formula

wherein all symbols have the same meanings as defined hereinbefore is reacted with compound [VII] to give compound [I$^a$]. This reaction can be conducted under the same conditions as process (C).

(E) When a compound of the formula [VI] wherein R$^{3a}$=H or a salt thereof is used as the starting material A compound of the formula

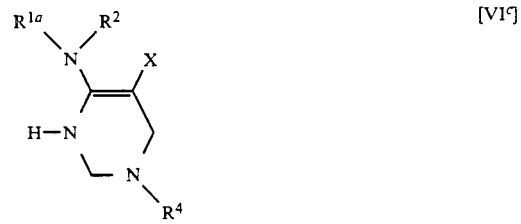

wherein all symbols have the same meanings as defined hereinbefore is reacted with compound [VII] to give compound [Iᵃ]. This reaction can be conducted under the same conditions as described for process (C).

(F) When a compound of the formula [VI] wherein R³ᵃ =R⁴=H or a salt thereof is used as the starting material A compound of the formula

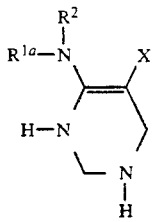

wherein all symbols have the same meanings as defined hereinbefore is reacted with compound [VII] to give compound [Iᵃ]. This reaction can also be conducted under the same conditions as described for process (C). However, the preferred proportion of compound [VII] based on compound [VIᵈ] is about 1.5 to 2.5 equivalents and when a base is used for promoting the reaction, the reaction is preferably carried out in the presence of about 1.5 to 3 equivalents of the base.

The compound [Iᵃ] or salt thus obtained can be isolated and purified by the per se known procedures such as concentration, concentration under reduced pressure, distillation, fractional distillation, solvent extraction, pH adjustment, redistribution, chromatography, crystallization, recrystallization and so on.

The compound [II], which is used as the starting material in the above method of the present invention, can be prepared by various processes, for example according to the following Scheme 1 and Scheme 2.

Scheme 1

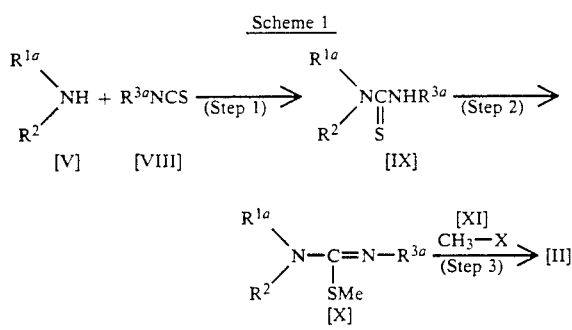

Scheme 2

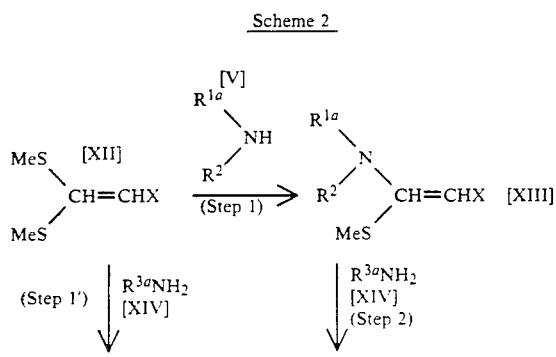

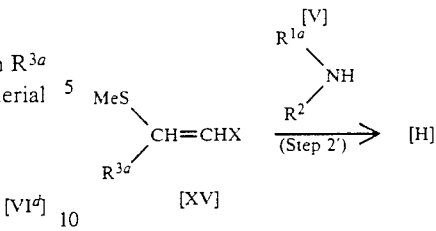

[In the above schematic representations, each symbol has the same meaning as defined hereinbefore]

The process according to Scheme 1

Step 1

Compound [V] is reacted with compound [VIII] either without using a solvent or in a solvent such as those mentioned for process (A) (preferably an aprotic solvent such as ether, THF, dichloromethane, chloroform, acetone, acetonitrile, toluene, etc.) to give compound [IX]. This reaction may be hastened by adding a base such as those mentioned for process (B). The reaction temperature and time are remarkably dependent on $R^{1a}$, $R^2$ and $R^{3a}$ but are preferably in the range of 0° to 130° C. and 10 minutes to 10 hours. Generally, about 0.8 to 1.5 equivalents of compound [VIII] is used to each equivalent of compound [V].

Step 2

Compound [IX] is reacted with a methylating agent such as methyl iodide, methyl bromide, dimethyl sulfate or the like to give compound [X]. This reaction is preferably conducted in a solvent such as those mentioned for process (A), and can be hastened by adding a base such as those mentioned for process (B). Generally the reaction temperature and time are 0° to 100° C. and 30 minutes to 10 hours. Based on compound [IX], the methylating agent is used generally in a proportion of 1.0 to 2.0 equivalents.

Step 3

Compound [X] is reacted with compound [XI] to give compound [II]. While this reaction can be conducted under the conditions described for process (B), the reaction temperature and time may be within the range of 80° to 150° C. and 5 to 100 hours. The reaction may be conducted using a solvent amount of compound [XI].

The process according to Scheme 2

Step 1

Based on compound [XII], compound [V] is used in a proportion of 0.8 to 1.5 equivalents. Generally, this reaction is carried out at 60° to 100° C. for 1 to 10 hours. The reaction is conducted under otherwise the same conditions as set forth for process (B) to give compound [XIII].

Step 2

Compound [XIII] is reacted with 0.8 to 5 equivalents of compound [XIV] to give compound [II]. This reaction can be conducted under otherwise the same conditions as set forth under Step 1.

Step 1' and Step 2'

These steps are carried out under the same conditions as described under Step 1 and Step 2 to give compound [XV] and compound [II], respectively.

The various compounds and the starting compounds [II] which can be obtained in the respective steps according to Schema 1 and Schema 2 can each be isolated and transferred to the next step but unless the next reaction is adversely affected, each reaction product mixture can be directly submitted to the next reaction.

Among the starting compounds to be used in the processes according to Schema 1 and Schema 2, compound [V] can be synthesized by the processes described in New Experimental Chemistry Series (Shin Jikken Kagaku Koza), Maruzen, Vol. 14-III, pp. 1332–1399 or any process analogous thereto and compound [VIII] can be synthesized by the processes described in New Experimental Chemistry Series, Maruzen, Vol. 14-III, pp. 1503–1509 or any process analogous thereto. Compound [XII] can be synthesized by the process described in Chemische Berichte 100, p.591 (1967) or any process analogous thereto, while compound [XIV] can be synthesized by the same processes mentioned for compound [V], for instance.

Referring to the starting compounds for use in the method of the invention, compound [III] can for example be synthesized by the processes described for compound [V]. Compound [IV], some species of which are known compounds, can be prepared by the process described in Journal of the Pharmaceutical Society of Japan 97, p.262 (1977) or any process analogous thereto, while compound [VII] can be synthesized by the processes described in New Experimental Chemistry Series, Maruzen, Vol. 14-I, pp. 307–450, Vol. 14-II, pp. 1120–1133, Vol. 14-III, pp. 1793–1798, etc. or any process analogous thereto.

It should be understood that compound [VI] and its species [VI$^a$], [VI$^b$], [VI$^c$] and [VI$^d$] are invariably subsumed in the category of compound [I$^a$] and, as such, can be prepared by the process (A) or (B) described hereinbefore for compound [I$^a$].

Activity

Tetrahydropyrimidine compound [I] and its salt have excellent pesticidal activity as evidenced by the following test examples.

TEST EXAMPLE 1

Effect on *Nilaparvata lugens*

Five milligrams each of test compounds (designated by Nos. assigned to the compounds prepared in Examples which appear hereinafter) were respectively dissolved in 0.5 ml of acetone containing Tween 20 ® and diluted with a 3,000-fold aqueous dilution of Dyne ® (a spreading agent manufactured by Takeda Chemical Industries, Ltd.) to a predetermined concentration of 500 ppm. Using a spray gun, this solution was applied to the stems and leaves of rice plant seedlings at the 2-leaf stage in paper nursery pots at the rate of 10 ml/pot. The bottom space of test tubes was filled with water and after the treated rice plant seedlings were put therein, 10 third-instar larvae of *Nilaparvata lugens* were released, followed by stoppering with an aluminum cap. Each test tube was held in an incubator at 25° C. and the deaths were counted 7 days after release. The mortality rate was calculated by means of the following equation.

$$\text{Mortality } (\%) = \frac{\text{Number of dead larvae}}{\text{Number of larvae released}} \times 100$$

TABLE 1

| Compound No. | Mortality (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 24 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 41 | 100 |
| 42 | 100 |
| 42 | 100 |
| 43 | 100 |
| 44 | 100 |
| 45 | 100 |
| 46 | 100 |
| 48 | 100 |
| 49 | 100 |
| 50 | 100 |
| 52 | 100 |
| 53 | 100 |
| 54 | 100 |
| 56 | 100 |
| 57 | 100 |
| 58 | 100 |
| 59 | 100 |

It is apparent from Table 1 that the tetrahydropyrimidine [I] and its salt have potent lethal effects on *Nilaparvata lugens*.

TEST EXAMPLE 2

Effects on *Spodoptera litura*

One milligram each of test compounds (designated by Nos. assigned to the compounds prepared in Examples which appear hereinafter) were respectively dissolved in 0.5 ml of acetone containing Tween 20 ® and diluted with a 3,000-fold aqueous dilution of Dyne ® to a concentration of 500 ppm. Using a spray gun, the solution was applied to young soybean plants (at the simple leaf unfolding stage) at the rate of 20 ml/pot. After the chemical solution had dried, two simple leaves of each plant were shorn off and put in an ice cream cup. Then, 10 third-instar larvae of *Spodoptera litura* were released per cup and the cup was left standing in a room (25° C.). After 2 days, dead larvae were counted and the mortality rate was calculated by means of the equation given in Test Example 1. The results are shown in Table 2.

TABLE 2

| Compound No. | Mortality (%) |
|---|---|
| 7 | 100 |
| 8 | 100 |
| 9 | 100 |
| 10 | 100 |
| 13 | 100 |
| 14 | 100 |
| 15 | 100 |
| 17 | 100 |
| 24 | 100 |
| 28 | 100 |
| 31 | 100 |
| 33 | 100 |
| 34 | 100 |
| 35 | 100 |
| 36 | 100 |
| 37 | 100 |
| 42 | 100 |
| 43 | 100 |
| 44 | 100 |
| 45 | 100 |
| 53 | 100 |
| 56 | 100 |
| 57 | 100 |
| 58 | 100 |
| 59 | 100 |

It is apparent from Table 2 that tetrahydropyrimidine [I] and its salt have potent lethal effects on *Spodoptera litura*.

The following examples and reference examples are intended to illustrate the invention in further detail and should by no means be construed as limiting the scope of the invention.

The procedure of elution in column chromatography as described in Examples and Reference Examples was invariably carried out under monitoring by thin layer chromatography (TLC). In TLC monitoring, Merck's Kieselgel 60F$_{254}$ (70–230 mesh) and the eluent for column chromatography were used as the TLC plate and the developer, respectively, and the UV detector was used for detection of spots. As the silica gel for column chromatography, Kieselgel 60 (70–230 mesh), also available from Merck, was used. The NMR spectra were recorded by proton NMR spectrometry using tetramethylsilane as the internal reference. The instrument used was Varian EM390 (90 MHz) spectrometer and all the δ values were expressed in ppm. The numerals given in parentheses for each solvent mixture used for elution represents the V/V ratio.

The abbreviations used in Examples, Reference Examples and Table 3 have the following meanings.

Me: methyl, Et: ethyl, n-Pr: n-propyl, i-Pr: isopropyl, t-Bu: t-butyl, Ph: phenyl, s: singlet, br: broad, d: doublet, t: triplet, q: quartet, m: multiplet, dd: double-doublet, J: coupling constant, Hz: Hertz, CDCl$_3$: deuterochloroform, DMSO-d$_6$: deuterated DMSO, %: weight %, Mp: melting point. The term 'room temperature' means a temperature between about 15° and 25° C.

REFERENCE EXAMPLE 1

On a water bath at 5°–20° C., a mixture of 70.3 g of 2-chloro-5-(hydroxymethyl)pyridine and 50 ml of 1,2-dichloroethane was added dropwise to a mixture of 87.4 g of thionyl chloride and 100 ml of 1,2-dichloroethane over a period of 30 minutes. The whole mixture was stirred at room temperature for 90 minutes and, then, under reflux for 4.5 hours. The reaction mixture was then concentrated and the residue was diluted with 200 ml of chloroform and 60 ml of water. Then, with stirring, 20 g of sodium hydrogen carbonate was added in small portions. Thereafter, the organic layer was separated, treated with activated carbon and concentrated to give 75.9 g of 2-chloro-5-(chloromethyl)pyridine as a yellow brown solid.

$^1$H NMR (CDCl$_3$): 4.57 (2H, s), 7.34 (1H, d, J=8.5 Hz), 7.72 (1H, dd, J=8.5, 2.5 Hz), 8.40 (1H, d, J=2.5 Hz).

REFERENCE EXAMPLE 2

A stainless steel autoclave was charged with 14.99 g of 2-chloro-5-(chloromethyl)pyridine, 63.01 g of 25% aqueous ammonia and 60 ml of acetonitrile and the mixture was stirred on an oil bath at 80° C. for 2 hours. The reaction mixture was diluted with 12.3 g of 30% aqueous sodium hydroxide solution and concentrated. The residue was diluted with 200 ml of ethanol, dried over anhydrous magnesium sulfate and filtered to remove the insolubles. Finally, the filtrate was concentrated and purified by column chromatography (eluent: dichloromethane-methanol (4:1)) to give 7.66 g of 5-(aminomethyl)-2-chloropyridine as a yellow solid.

$^1$H NMR (CDCl$_3$): 1.60 (2H, s), 3.90 (2H, s), 7.28 (1H, d, J=8.5 Hz), 7.67 (1H, dd, J=8.5, 2.5 Hz), 8.33 (1H, d, J=2.5 Hz)

In substantially the same manner as above, 5-(aminomethyl)-2-bromopyridine, 5-(aminomethyl)-2-chlorothiazole and 5-(aminomethyl)-2-(4-chlorophenoxy)pyridine were obtained.

REFERENCE EXAMPLE 3

A mixture of 15.05 g of 2-chloro-5-(chloromethyl)pyridine and 50 ml of acetonitrile was added dropwise to a mixture of 36 g of 40% aqueous methylamine solution and 200 ml of acetonitrile over a period of 1 hour at room temperature and the whole mixture was further stirred for 90 minutes. The reaction mixture was concentrated and the residue was diluted with 100 ml of water, neutralized with sodium hydrogen carbonate, saturated with sodium chloride and extracted with dichloromethane (200 ml×2). The organic solution was dried over anhydrous magnesium sulfate and concentrated and the residue was purified by column chromatography (eluent: dichloromethane-methanol (4:1)) to give 8.77 g of 2-chloro-5-(methylaminomethyl)pyridine as a yellow brown liquid.

$^1$H NMR (CDCl$_3$): 1.30 (1H, br, s), 2.44 (3H, s) 3.75 (2H, s), 7.30 (1H, d, J=8.4 Hz), 7.68 (1H, dd, J=8.4, 2.4 Hz), 8.35 (1H, d, J=2.4 Hz).

In substantially the same manner, 2-chloro-5-(ethylaminomethyl)pyridine, 2-chloro-5-(isopropylaminomethyl)pyridine, 2-(4-chlorophenoxy)-5-(ethylaminomethyl)pyridine and 3-(methylaminomethyl)pyridine were prepared.

REFERENCE EXAMPLE 4

On a water bath at about 20° C., a solution of 1.44 g of methyl isothiocyanate in 2 ml of dichloromethane was added dropwise to a mixture of 2.81 g of 2-chloro-5-(methylaminomethyl)pyridine and 10 ml of dichloromethane over a period of 10 minutes and the whole mixture was further stirred for 30 minutes. The reaction mixture was then concentrated and the residue was purified by column chromatography (eluent: dichloromethane-methanol (20:1)) to give 3.33 g of 1-(6-chloro-3-pyridylmethyl)-1,3-dimethylthiourea.

To a mixture of 2.56 g of the above thiourea and 20 ml of THF was added 0.294 g of sodium hydride (in oil, 60%) in small portions with ice-cooling and the mixture was stirred for 30 minutes. Then, under ice-cooling, a solution of 1.74 g of iodomethane in 2 ml of THF was added dropwise over 5 minutes and the mixture was stirred at room temperature for 3 hours. The reaction mixture was then concentrated, diluted with 50 ml of dichloromethane, and washed with water. The organic layer was concentrated and, after addition of 200 ml of nitromethane, the solution was refluxed for 12 hours. The reaction mixture was concentrated and purified by column chromatography (eluent: dichloromethane-methanol (9:1)) to give 1.63 g of 1-[N-(6-chloro-3-pyridylmethyl)-N-methylamino]-1-methylamino-2-nitroethylene Mp 103°-104° C.

In substantially the same manner as described above, the following compounds were obtained:
1-[N-(6-Chloro-3-pyridylmethyl)-N-ethylamino]-1-methylamino-2-nitroethylene,
1-[N-(6-chloro-5-pydidylmethyl)-N-isopropylamino]-1-methylamino-2-nitroethylene,
1-[N-(6-chloro-3-pyridyl)-N-methylamino]-1-methylamino-2-nitroethylene and
1-[N-[6-(4-chlorophenoxy)-3-pyridylmethyl]-N-ethylamino]-1-methylamino-2-nitroethylene.

REFERENCE EXAMPLE 5

To a refluxing mixture of 6.61 g of 1,1-bis(methylthio)-2-nitroethylene and 100 ml of acetonitrile was added a solution of 4.28 g of 5-aminomethyl-2-chloropyridine in 10 ml of acetonitrile dropwise over a period of 3 hours and 30 minutes and the whole mixture was further refluxed for 2 hours. After cooling, the insolubles (by-product; 1,1-bis(6-chloro-3-pyridylmethylamino)-2-nitroethylene) were filtered off and the filtrate was concentrated and washed with ethyl acetate to give 4.83 g of 1-(6-chloro-3-pyridylmethylamino)-1-methylthio-2-nitroethylene. The ethyl acetate washings were concentrated and the residue was purified by column chromatography (eluent: dichloromethane-methanol (30:1)) to give a further crop (1.15 g) of the same compound.

In substantially the same manner as above, the following compounds were obtained:
1-[N (6 Chloro-3-pyridylmethyl)-N-methylamino]-1-methylthio-2-nitroethylene,
1-[N-(6-chloro-3-pyridylmethyl)-N-ethylamino]-1-methylthio-2-nitroethylene,
1-(N-methyl-N-pyridylmethylamino)-1-methylthio-2-nitroethylene,
1-(6-bromo-3-pyridylmethylamino)-1-methylthio-2-nitroethylene,
1-[6-(4-chlorophenoxy)-3-pyridylmethylamino]-1-methylthio-2-nitroethylene,
1-(6-chloro-3-pyridylamino)-1-methylthio-2-nitroethylene
1-methylthio-1-(3-pyridylmethylamino)-2-nitroethylene and
1-(2-chloro-5-thiazolylmethylamino)-1-methylthio-2-nitroethylene.

REFERENCE EXAMPLE 6

A mixture of 2.0 g of 1-(6-chloro-3-pyridylmethylamino)-1-methylthio-2-nitroethylene, 1.8 g of 40% aqueous methylamine solution and 20 ml of acetonitrile was refluxed for 3 hours and, then concentrated. The residue was washed with dichloromethane to give 1.73 g of 1-(6-chloro-3-pyridylmethylamino)-1-methylamino-2-nitroethylene. Mp 181°-183° C.

In substantially the same manner as above, the following compounds were obtained:
1 (6-Chloro-3-pyridylmethylamino)-1-dimethylamino-2-nitroethylene,
1-(6-chloro-3-pyridylmethylamino)-1-ethylamino-2-nitroethylene,
1,1-bis(6-chloro-3-pyridylmethylamino)-2-nitroethylene,
1-amino-1-(6-chloro-3-pyridylmethylamino)-2-nitroethylene,
1-(6-chloro-3-pyridylmethylamino)-1-isopropylamino-2-nitroethylene,
1-amino-1-[N-(6-chloro-3-pyridylmethyl)-N methylamino]-2-nitroethylene,
1-amino-1-[N-(6-chloro-3-pyridylmethyl)-N-ethylamino]-2-nitroethylene,
1-amino-1-(N-methyl-N-pyridylmethylamino)-2-nitroethylene,
1-(6-bromo-3-pyridylmethylamino)-1-methylamino-2-nitroethylene,
1-[6-(4-chlorophenoxy)-3-pyridylmethylamino]-1-methylamino-2-nitroethylene,
1-(6-chloro-pyridylamino)-1-methylamino-2-nitroethylene,
1-amino-1-(3-pyridylmethylamino)-2-nitroethylene and
1-(2-chloro-5-thiazolylmethylamino)-1-methylamino-nitroethylene.

REFERENCE EXAMPLE 7

To a mixture of 5.93 g of 1-methylamino-1-methylthio-nitroethylene, 7.15 g of 37% formalin and 100 ml of acetonitrile was added a solution of 3.42 g of 40% aqueous methylamine in 10 ml of acetonitrile dropwise over a period of 90 minutes with ice-cooling and the whole mixture was stirred at room temperature for 8 hours and, then, allowed to stand overnight. The reaction mixture was concentrated and purified by column chromatography (eluent: dichloromethane-methanol (20:1)) to give 5.82 g of 1,3-dimethyl-4-methylthio-5-nitro-1,2,3,6-tetrahydropyrimidine as a syrup.

$^1$HNMR(COCl$_3$): 2.43 (3H, s), 2.50 (3H, s), 3.29 (3H, s), 3.77 (2H, s), 3.86 (2H, s).

In substantially the same manner as above, the following compounds were obtained:
1-Ethyl-3-methyl-4-methylthio-5-nitro-1,2,3,6-tetrahydropyrimidine,
3-methyl-4-methylthio-5-nitro-1-propyl-1,2,3,6-tetrahydropyrimidine,
1-isopropyl-3-methyl-4-methylthio-5-nitro-1,2,3,6-tetrahydropyrimidine,
3-methyl-4-methylthio-5-nitro-1-phenyl-1,2,3,6-tetrahydropyrimidine,
3-ethyl-1-methyl-4-methylthio-5-nitro-1,2,3,6-tetrahydropyrimidine,
3-(6-chloro-3-pyridylmethyl)-1-methyl-4-methylthio-5-nitro-1,2,3,6-tetrahydropyrimidine,
3-(6-chloro-3-pyridylmethyl)-1-ethyl-4-methylthio-5-nitro-1,2,3,6-tetrahydropyrimidine and
4-methylthio-5-nitro-1,3-bis(3-pyridylmethyl)-1,2,3,6-tetrahydropyrimidine.

EXAMPLE 1

To a mixture of 0.898 g of 1-[N-(6-chloro-3-pyridylmethyl)-N-methylamino]-1-methylamino-2-nitroethylene, 0.31 g of 40% aqueous methylamine, 5 ml of ethanol and 5 ml of THF was added 0.601 g of 37% formalin dropwise over 20 minutes with ice-cooling and the whole mixture was further stirred at room temperature overnight. The reaction mixture was then concentrated and purified by column chromatography (eluent: dichloromethane-methanol (10:1)) to give 1.00 g of 4-[N-(6-chloro-3-pyridylmethyl)-N-methylamino]-1,3-dimethyl-5-nitro-1,2,3,6-tetrahydropyrimidine (Compound No. 1) as a syrup.

Elemental analysis ($C_{13}H_{18}N_5O_2Cl$). Calcd. C: 50.08, H: 5.82, N: 22.46. Found C: 49.94, H: 5.60, N: 22.62.

$^1$H NMR (CDCl$_3$): 2.44 (3H, s), 2.80 (3H, s), 3.08 (3H, s), 3.60 (2H, s), 3.69 (2H, s), 4.1–4.6 (2H, m), 7.36 (1H, d, J=8.5 Hz), 7.73 (1H, dd, J =8.5, 2.5 Hz), 8.34 (1H, d, J=2.5 Hz).

EXAMPLE 2

To a mixture of 0.52 g of 1-(6-chloro-3-pyridylmethylamino)-1-methylamino-2-nitroethylene, 0.20 g of t-butylamine and 5 ml-of acetonitrile was added 0.50 g of 37% formalin dropwise over a period of 10 minutes with ice cooling and the mixture was stirred under ice cooling for 1 hour and, then, at room temperature for 2 hours and 30 minutes. The reaction mixture was then concentrated and the residue was purified by column chromatography (eluent: ethyl acetate) to give 0.52 g of a mixture of 1-t-butyl-4-(6-chloro-3-pyridylmethylamino)-3-methyl-5-nitro-1,2,3,6-tetrahydropyrimidine (Compound No. 17) and 1-t-butyl-3-(6-chloro-3-pyridylmethyl)-4-methylamino-5-nitro-1,2,3,6-tetrahydropyrimidine (Compound No. 44). This mixture was further purified by column chromatography to give Compound No. 44 and Compound No. 17 (eluted in the order mentioned).

Compound No. 17: Mp 169°–170° C.

$^1$H NMR (δ, CDCl$_3$): 1.13 (9H, s), 2.97 (3H, s), 3.63 (2H, s), 3.72 (2H, s), 4.53 (2H, d, J=6.0 Hz), 7.35 (1H, d, J=8.5 Hz}, 7.73 (2H, dd, J=8.5, 2.5 Hz), 8.37 (1H, d, J=8.5 Hz), 10.43 (1H, br, t, J=6 Hz).

Compound No. 44: Mp 160°–161° C.

$^1$H NMR (δ, CDCl$_3$): 1.04 (9H, s), 3.03 (3H, d, J=6 Hz), 3.55 (2H, s), 3.72 (2H, s), 4.36 (2H, s), 7.40 (1H, d, J=8.5 Hz), 7.75 (1H, dd, J=8.5 Hz, 2.5 Hz), 8.45 (1H, d, J=2.5 Hz), 10.42 (1H, br. s)

EXAMPLE 3

A mixture of 0.61 g of 1,3-dimethyl-4-methylthio-5-nitro-1,2,3,6-tetrahydropyridylmethylamine, 0.357 g of 3 pyridylmethylamine and 6 ml of acetonitrile was stirred at room temperature for 5 hours. The reaction mixture was then concentrated and purified by column chromatography (eluent: dichloromethane-methanol (10:1)) to give 0.33 g of 1,3-dimethyl-4-(pyridylmethylamino)-5 nitro-1,2,3,6-tetrahydropyrimidine (Compound No. 31) as a syrup.

Elemental analysis ($C_{12}H_{17}N_5O_2$). Calcd. C: 54.74, H: 6.51, N: 26.60. Found C: 54.62, H: 6.36, N: 26.41.

$^1$H NMR (CDCl$_3$): 2.39 (3H, s), 3.12 (3H, s), 3.67 (2H, s), 3.78 (2H, s), 4.59 (2H, d, J=5.7 Hz), 7.2–7.45 (1H, m), 7.65–7.85 (1H, m), 8.5–8.7 (2H, m), 10.86 (1H, br, t, J=5.7 Hz).

EXAMPLE 4

To a mixture of 0.27 g of 4-(6-chloro-3-pyridylmethylamino)-1,3-dimethyl-5-nitro-1,2,3,6-tetrahydropyrimidine (Compound No. 13), 5 ml of dry THF and 5 ml of dry acetonitrile was added 0.0239 g of sodium hydride (60%, in oil) in small portions over 1 minute with ice cooling. After the mixture was stirred at room temperature for 30 minutes, a solution of 0.24 g of formic acetic anhydride in 1 ml of THF was added dropwise over a period of 4 minutes with ice cooling and the mixture was then stirred at room temperature for 3 hours. The reaction mixture was concentrated and purified by column chromatography (eluent: dichloromethane-methanol (20:1)) to give 0.14 g of 4-[N-(6-chloro-3-pyridylmethyl)-N-formylamino]-1,3-dimethyl-5-nitro-1,2,3,6-tetrahydropyrimidine (Compound No. 30) as a syrup.

$^1$H NMR (δ, CDCl$_3$): 2.41 (3H, s), 2.93 (3H, s), 3.6–4.0 (4H, m), 4.63 (1H, d, J=14.7 Hz), 4.87 (1H, d, J=14.7 Hz), 7.33 (1H, d, J=8.5 Hz), 7.78 (1H, dd, J=8.5, 2.5 Hz), 8.21 (1H, s), 8.32 (1H, d, J=2.5 Hz).

The compounds listed below in Table 3 were produced by the production processes of the invention or in accordance with Examples 1 through 4. The list in Table 3 includes the compounds obtained in Examples 1 through 4.

Among the listed compounds, preferable compounds can be represented by the formula,

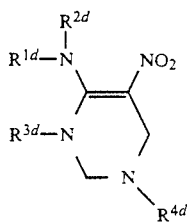

wherein one of $R^{1d}$ and $R^{3d}$ is $R^{5b}$—CH$_2$— (wherein $R^{5b}$ is a halopyridyl or halothiazolyl group) and the other is H or a $C_{1-3}$ alkyl group, $R_{2d}$ is H or a $C_1$–$C_3$ alkyl group and R4d is a $C_1$–$C_4$ alkyl or $C_{7-10}$ aralkyl group.

The examples of the preferable compounds in Table 3 include the compounds of No. 13, 15, 28, 33, 34, 43, 44, 45, and 53, and most preferable is No. 45.

TABLE 3

$$\begin{array}{c} R^2 \\ | \\ R^1-N \end{array} \begin{array}{c} NO_2 \\ \diagup \\ R^3-N \end{array} \diagdown N-R^4$$

| Compound No. | R¹ | R² | R³ | R⁴ | MP (°C.) | Process (corresponding Example No.) |
|---|---|---|---|---|---|---|
| 1 | 6-Cl-pyridin-3-yl-CH₂ | Me | Me | Me | (Syrup)ᵃ⁾ | 1 |
| 2 | 6-Cl-pyridin-3-yl-CH₂ | Me | Me | t-Bu | 147–150 | 1 |
| 3 | 6-Cl-pyridin-3-yl-CH₂ | Me | Me | cyclohexyl | 131–133 | 1 |
| 4 | 6-Cl-pyridin-3-yl-CH₂ | Me | Me | CH₂Ph | 152–155 | 1 |
| 5 | 6-Cl-pyridin-3-yl-CH₂ | Et | Me | Me | (Syrup)ᵇ⁾ | 1 |
| 6 | 6-Cl-pyridin-3-yl-CH₂ | i-Pr | Me | CH₂CF₃ | 115–120 | 1 |

TABLE 3-continued $$\begin{array}{c} R^2 \\ | \\ R^1-N \\ \diagdown \\ \end{array} \begin{array}{c} NO_2 \\ \| \\ \diagup \\ R^3-N \end{array} \begin{array}{c} \\ \diagdown \\ N-R^4 \\ \diagup \end{array}$$

| Compound No. | R¹ | R² | R³ | R⁴ | MP (°C.) | Process (corresponding Example No.) |
|---|---|---|---|---|---|---|
| 7 | 2-chloro-5-pyridylmethyl | Me | Me | Me | 139–140 | 1 |
| 8 | 2-chloro-5-pyridylmethyl | Me | Me | Et | 82.5–83 | 1 |
| 9 | 2-chloro-5-pyridylmethyl | Me | Me | cyclopropyl | 152–152.5 | 1 |
| 10 | 2-chloro-5-pyridylmethyl | Me | Me | CH₂CH₂OH | 120 | 1 |
| 11 | 2-(4-chlorophenoxy)-5-pyridylmethyl | Et | Me | Me | (Syrup)ᵇ | 1 |
| 12 | Me | Me | 2-chloro-5-pyridylmethyl | Me | (Syrup)ᵇ | 1 |

TABLE 3-continued
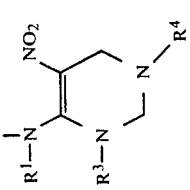
| Compound No. | R¹ | R² | R³ | R⁴ | MP (°C.) | Process (corresponding Example No.) |
|---|---|---|---|---|---|---|
| 13 |  | H | Me | Me | 144-145 | 3 |
| 14 |  | H | Me | Et | 119-121 | 3 |
| 15 |  | H | Me | n-Pr | 103-108 | 3 |
| 16 |  | H | Me | i-Pr | (Syrup)$^{b)}$ | 3 |
| 17 |  | H | Me | t-Bu | 169-170 | 2 |
| 18 | | H | Me | Ph | 193-195 (decomposition) | 3 |

TABLE 3-continued

Structure: R¹–N(R²)–C(=C(NO₂)–CH₂–N(R⁴)–CH₂)–N(R³)

| Compound No. | R¹ | R² | R³ | R⁴ | MP (°C.) | Process (corresponding Example No.) |
|---|---|---|---|---|---|---|
| 19 | 6-chloro-pyridin-3-yl-CH₂ | H | Me | CH₂Ph | 146–150 | 2 |
| 20 | 6-chloro-pyridin-3-yl-CH₂ | H | Et | Me | 135–138 | 3 |
| 21 | 6-chloro-pyridin-3-yl-CH₂ | H | Et | Et | 95–101 | 2 |
| 22 | 6-chloro-pyridin-3-yl-CH₂ | H | 6-chloro-pyridin-3-yl-CH₂ | Me | 150–153 | 1 |
| 23 | 6-chloro-pyridin-3-yl-CH₂ | H | 6-chloro-pyridin-3-yl-CH₂ | Et | 164–165 (decomposition) | 1 |
| 24 | 6-chloro-pyridin-3-yl-CH₂ | H | Me | 6-chloro-pyridin-3-yl-CH₂ | 198–200 (decomposition) | 2 |

TABLE 3-continued $$\begin{array}{c} R^2 \\ | \\ R^1-N \quad NO_2 \\ \diagdown \quad | \\ C=C \\ / \quad \diagdown \\ R^3-N \quad CH_2 \\ \diagdown \quad / \\ CH_2-N-R^4 \end{array}$$

| Compound No. | R¹ | R² | R³ | R⁴ | MP (°C.) | Process (corresponding Example No.) |
|---|---|---|---|---|---|---|
| 25 | 6-chloro-3-pyridylmethyl | H | Me | H | — | 2 |
| 26 | 6-chloro-3-pyridylmethyl | H | H | Me | 185–187 | 2 |
| 27 | 6-chloro-3-pyridylmethyl | H | i-Pr | 6-chloro-3-pyridylmethyl | (Syrup)[h] | 2 |
| 28 | 6-chloro-3-pyridylmethyl | Me | H | Me | 130–131 | 1 |
| 29 | 6-chloro-3-pyridylmethyl | Et | H | Me | 134–136 | 1 |
| 30 | 6-chloro-3-pyridylmethyl | CHO | Me | Me | (Syrup)[c] | 4 |

TABLE 3-continued $$\begin{array}{c} R^2 \\ | \\ R^1-N \\ \phantom{R^1-}\diagdown C=C\diagup NO_2 \\ \phantom{R^1-N\diagdown}| \phantom{=} | \\ \phantom{R^1-N\diagdown}R^3-N\phantom{=}CH_2 \\ \phantom{R^1-N\diagdown R^3-}\diagdown CH_2\diagup \\ \phantom{R^1-N\diagdown R^3-N\diagdown CH_2}| \\ \phantom{R^1-N\diagdown R^3-N\diagdown CH}R^4 \end{array}$$

| Compound No. | R¹ | R² | R³ | R⁴ | MP (°C.)$^{(a)}$ | Process (corresponding Example No.) |
|---|---|---|---|---|---|---|
| 31 | 3-pyridylmethyl (CH₂-pyridine) | H | Me | Me | (Syrup)$^d$ | 3 |
| 32 | 3-pyridylmethyl | Me | H | Me | 149–150 | 2 |
| 33 | (6-bromo-3-pyridyl)methyl | H | Me | Me | 140–143 | 2 |
| 34 | (2-chloro-1,3-thiazol-5-yl)methyl | H | Me | Me | 134–137 | 2 |
| 35 | (2-chloro-1,3-thiazol-5-yl)methyl | H | Me | Et | (Syrup)$^b$ | 2 |
| 36 | (2-chloro-1,3-thiazol-5-yl)methyl | H | Me | PhCH₂ | 143–143.5 | 2 |

TABLE 3-continued

R¹-N(R²)-C(=C(NO₂))-N(R³)-CH₂CH₂-N(R⁴)... (structure shown)

| Compound No. | R¹ | R² | R³ | R⁴ | MP (°C.) | Process (corresponding Example No.) |
|---|---|---|---|---|---|---|
| 37 | 2-chloro-thiazol-5-yl-CH₂ | H | Me | 4-methylphenyl-CH₂ | 116–119 | 2 |
| 38 | 4-chlorophenyl-CH₂ | H | Me | Me | 147–149 | 3 |
| 39 | 3,4-dichlorophenyl-CH₂ | H | Me | Me | 125–129 | 3 |
| 40 | 6-(4-chlorophenoxy)-pyridin-3-yl-CH₂ | H | Me | Me | 116–117 | 2 |
| 41 | PhCH₂ | H | PhCH₂ | PhCH₂ | 112–115 | 1 |
| 42 | Me | H | 6-chloro-pyridin-3-yl-CH₂ | Me | 141–145 | 3 |
| 43 | Me | H | 6-chloro-pyridin-3-yl-CH₂ | Et | 152–153 | 3 |

TABLE 3-continued
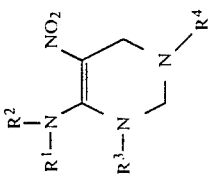
| Compound No. | R¹ | R² | R³ | R⁴ | MP (°C.) | Process (corresponding Example No.) |
|---|---|---|---|---|---|---|
| 44 | Me | H | 6-chloro-pyridin-3-yl-CH₂ | t-Bu | 160–161 | 2 |
| 45 | Me | H | 6-chloro-pyridin-3-yl-CH₂ | CH₂Ph | 168–171 | 2 |
| 46 | Me | H | 6-chloro-pyridin-3-yl-CH₂ | 6-chloro-pyridin-3-yl-CH₂ | 191–193 (decomposition) | 2 |
| 47 | Me | H | 6-chloro-pyridin-3-yl-CH₂ | H | | 2 |
| 48 | Et | H | 6-chloro-pyridin-3-yl-CH₂ | Et | 91–96 | 2 |
| 49 | i-Pr | H | 6-chloro-pyridin-3-yl-CH₂ | Me | (Syrup)[b] | 2 |

TABLE 3-continued

| Compound No. | R¹ | R² | R³ | R⁴ | MP (°C.)[b] | Process (corresponding Example No.) |
|---|---|---|---|---|---|---|
| 50 | i-Pr | H | 6-Cl-pyridin-3-yl-CH₂ | 6-Cl-pyridin-3-yl-CH₂ | (Syrup)[b] | 2 |
| 51 | H | H | 6-Cl-pyridin-3-yl-CH₂ | Me | 158–160 | 2 |
| 52 | Me | H | 6-Cl-pyridin-3-yl-CH₂ | Me | 141–142 (decomposition) | 1 |
| 53 | Me | H | 6-Br-pyridin-3-yl-CH₂ | Me | 157–159 | 2 |
| 54 | Me | H | pyridin-3-yl-CH₂ | pyridin-3-yl-CH₂ | 146–147 | 3 |
| 55 | Me | H | 6-(4-chlorophenoxy)pyridin-3-yl-CH₂ | Me | 167–168 | 2 |

TABLE 3-continued $$R^1-N(R^2)-C(=C(NO_2)-CH_2-N(R^4)-...)-N(R^3)-CH_2$$

| Compound No. | $R^1$ | $R^2$ | $R^3$ | $R^4$ | MP (°C.) | Process (corresponding Example No.) |
|---|---|---|---|---|---|---|
| 56 | Me | H | 2-chloro-thiazol-5-ylmethyl | Me | 152–154 | 2 |
| 57 | Me | H | 2-chloro-thiazol-5-ylmethyl | Et | 120.5–124.5 | 2 |
| 58 | Me | H | 2-chloro-thiazol-5-ylmethyl | PhCH$_2$ | 171.5–173.5 | 2 |
| 59 | Me | H | 2-chloro-thiazol-5-ylmethyl | 4-MeC$_6$H$_4$CH$_2$ | 165–167 | 2 |
| 60 | H | H | 3-pyridylmethyl | Et | | 3 | a) 1HNMR: presented in Example 1.
b) 1HNMR: presented in Table 4.
c) 1HNMR: presented in Example 4.
d) 1HNMR: presented in Example 2.

TABLE 4

| Compound No. | $^1$HNMR (in CDCl$_3$) |
|---|---|
| 5 | 1.18(3H, t, J=7.0Hz), 2.40(3H, s), 3.02(3H, s), 3.22(2H, q, J=7.0Hz), 3.59(4H, s), 4.00–4.67(2H, m), 7.33(1H, d, J=8.5Hz), 7.72(1H, dd, J=8.5, 2.5Hz), 8.32(1H, d, J=2.5Hz) |
| 11 | 1.17(3H, t, J=7.2Hz), 2.41(3H, s), 2.7–3.4(5H, m), 3.62(4H, s), 4.0–4.7(2H, m) 6.93(1H, d, J=8.5Hz), 7.0–7.2(2H, m), 7.25–7.45(2H, m), 7.73(1H, dd, J=8.5, 2.5Hz), 8.09(1H, d, J=2.5Hz) |
| 12 | 2.39(3H, s), 2.87(6H, s), 3.51(2H, s), 3.58(2H, s), 4.43(2H, s), 7.33(1H, d, J=8.1Hz), 7.71(1H, dd, J=8.1, 2.7hz), 8.38(1H, d, J=2.7Hz) |
| 16 | 1.07(6H, d, J=6.5Hz), 2.4–3.1(1H, m), 3.05(3H, s), 3.73(2H, s), 3.77(2H, s), 4.57(2H, d, J=6.0Hz), 7.35(1H, d, J=8.4Hz), 7.73(1H, dd, J=8.4, 2.5Hz), 8.38(1H, d, J=2.5Hz), 10.67(1H, br.t, J=6.0Hz) |
| 27 | 1.19(6H, d, J=7.0Hz), 3.38(4H, s), 3.57(2H, s), 4.00(1H, m), 4.47(2H, d, J=6.0Hz), 7.27(2H, d, J=8.5Hz), 7.63(2H, dd, J=8.5, 2.5Hz), 8.30(2H, d, J=2.5Hz), 10.43(1H, t, J=6.0Hz) |
| 35 | 1.14(3H, t, J=7.0Hz), 2.55(2H, q, J=7.0Hz), 3.08(3H, s), 3.69(2H, s), 3.79(2H, s), 4.62(2H, d, J=6.0Hz), 7.50(1H, s), 10.51(1H, br.t, J=6.0Hz) |
| 49 | 1.26(6H, d, J=6.0Hz), 2.37(3H, s), 3.50(2H, s), 3.58(2H, s), 3.9–4.3(1H, m), 4.47(2H, s), 3.9–4.3 (1H, m), 7.40(1H, d, J=8.5Hz), 7.67(1H, dd, J=8.5, 2.5Hz), 8.37(1H, d, J=2.5Hz), 10.07(1H, d, J=8.5Hz) |
| 50 | 1.28(6H, d, J=6.0Hz), 3.51(2H, s), 3.6–3.9(5H, m), 4.37(2H, s), 7.28(1H, d, J=8.5Hz), 7.32(1H, d, J=8.5Hz), 7.48(1H, dd, J=8.5, 2.5Hz), 7.53(1H, dd, J=8.5, 2.5Hz), 8.30(2H, d, J=2.5Hz), 9.97(1H, d, J=9.0Hz) |

EXAMPLE 5

An emulsifiable concentrate was prepared by mixing Compound No. 2 (20% by weight), xylene (75% by weight) and polyoxyethylene glycol ether (Nonipol85®) (5% by weight).

EXAMPLE 6

A wettable powder was prepared by mixing Compound No. 7 (30% by weight), sodium ligninsulfonate (5% by weight), polyoxyethylene glycol ether (Nonipol 85®) (5% by weight), white carbon (30% by weight) and clay (30% by weight).

EXAMPLE 7

A dust was prepared by mixing Compound No 13 (3% by weight), white carbon (3% by weight) and clay (94% by weight).

EXAMPLE 8

Granules were prepared by milling Compound No. 17 (10% by weight), sodium ligninsulfonate (5% by weight) and clay (85% by weight) together, kneading the mixture well with water, granulating it and drying the granules.

What is claimed is:

1. A method for combatting insect pests which comprises administration of an insecticidally effective amount of a composition comprising:
(a) a compound of the formula

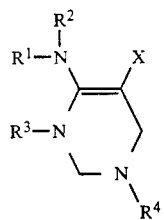

or a salt thereof as an active ingredient,
wherein $R^1$, $R^2$, $R^3$ and $R^4$ are the same or different and are each independently selected from the group consisting of:
a hydrogen atom;
a hydrocarbon group selected from the group consisting of an alkyl group of 1 to 15 carbon atoms, a cycloalkyl group of 3 to 10 carbon atoms, an alkenyl group of 2 to 10 carbon atoms, an alkynyl group of 2 to 20 carbon atoms, a cycloalkenyl group of 3 to 10 carbon atoms, an aryl group of 6 to 10 carbon atoms, and an aralkyl group of 7 to 10 carbon atoms, said hydrocarbon group being unsubstituted or substituted with 1 to 5 substituents selected from the group consisting of nitro, hydroxyl, oxo, thioxo, cyano, carbamoyl, carboxyl, $C_{1-4}$ alkoxycarbonyl, sulfo, halogen, $C_{1-4}$ alkoxy, phenoxy, $C_{1-4}$ alkylthio, phenylthio, $C_{1-4}$ alkylsulfinyl, $C_{1-4}$ alkylsulfonyl, amino, $C_{2-6}$ acylamino, methylamino, ethylamino, n-propylamino, isopropylamino, n-butylamino, dimethylamino, diethylamino, cyclohexylamino, anilino, $C_{2-4}$ acyl, benzoyl and a heterocyclic group selected from the group consisting of 2-thienyl, 3-thienyl, 2-furyl, 3-furyl, 3-pyrazolyl, 4-pyrazolyl, 5-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isooxazolyl, 4-isooxazolyl, 5-isooxazolyl, 2-imidazolyl, 4-imidazolyl, 5-imidazolyl, 1,2,3-triazolyl, 1,2,4-triazolyl, 1H-tetrazolyl, 2H-tetrazolyl, 2-pyridyl, 3-pyridyl, 4-pyridyl, 2-pyrimidyl, 4-pyrimidyl, 5-pyrimidyl, 3-pyridazinyl, 4-pyridazinyl, quinolyl, isoquinolyl and indolyl, said heterocyclic group being unsubstituted or substituted with 1 to 4 substituents selected from the group consisting of a halogen atom, $C_{1-4}$ alkyl, halophenoxy and halo $C_{1-4}$ alkyl, and when said hydrocarbon group is said aryl, aralkyl, cycloalkyl or cycloalkenyl group, said substituents further including a member selected from the group consisting of an alkyl group of 1 to 15 carbon atoms, an alkenyl group of 2 to 10 carbon atoms, an alkynyl group of 2 to 20 carbon atoms and an aryl group of 6 to 10 carbon atoms; and
a five- to eight-membered heterocyclic ring or a fused ring derivative thereof selected from the group consisting of 2-thienyl, 3-thienyl, 2-furyl, 3-furyl, 2-pyrrolyl, 3-pyrrolyl, 2-pyridyl, 3-pyridyl, 4-pyridyl, 2-oxazolyl, 4-oxazolyl, 5-oxazolyl, 2-thiazolyl, 4-thiazolyl, 5-thiazolyl, 3-pyrazolyl, 4-pyrazolyl, 5-pyrazolyl, 2-imidazolyl, 4-imidazolyl, 5-imidazolyl, 3-isooxazolyl, 4-isooxazolyl, 5-isooxazolyl, 3-isothiazolyl, 4-isothiazolyl, 5-isothiazolyl, 3-(1,2,4-oxadiazolyl), 5-(1,2,4-oxadiazolyl), 1,3,4-oxadiazolyl, 3-(1,2,4-thiadiazolyl), 5-(1,2,4-thiadiazolyl), 1,3,4-thiadiazolyl, 4-(1,2,3-thiadiazolyl), 5(1,2,3-thiadiazolyl), 1,2,5-thiadiazolyl, 1,2,3-triazolyl, 1,2,4-triazolyl, 1H-tetrazolyl, 2H-tetrazolyl, N-oxido-2,3,-pyridyl, N-oxido-4-pyridyl, 2-pyrimidyl, 4-pyrimidyl, 5-pyrimidyl, N-oxido-2-pyrimidyl, N-oxido-4-pyrimidyl, N-oxido-5-pyrimidyl, 3-pyridazinyl, 4-pyridazinyl, pyrazinyl, N-oxido-3-pyridazinyl, N-oxido-4-pyridazinyl, benzofuryl, benzothiazolyl, benzoxazolyl, triazinyl, oxotriazinyl, tetrazolo(1,5-b)pyridazinyl, triazolo(4,5-b)pyridazinyl, oxoimidazinyl, dioxotriazinyl, pyrrolidinyl, piperidinyl, pyranyl, thiopyranyl, 1,4-oxazinyl, morpholinyl, 1,4-thiazinyl, 1,3-thiazinyl, piperazinyl, benzimidazolyl, quinolyl, isoquinolyl, cinnolinyl, phthalazinyl, quinazolinyl, quinoxalinyl, indolidinyl, quinolidinyl, 1,8-naphthyridinyl, purinyl, pteridinyl, dibenzofuranyl, carbazolyl, acridinyl, phenanthridinyl, phenazinyl, phenothiazinyl and phenoxazinyl, said heterocyclic ring or fused ring derivative thereof being unsubstituted or substituted with 1 to 5 substituents selected from the group consisting of said substituents for said hydrocarbon group;

and X represents an electron accepting group selected from the group consisting of cyano, nitro, $C_{1-4}$ alkoxycarbonyl, hydroxycarbonyl, $C_{6-10}$ aryloxycarbonyl, pyridyloxycarbonyl, thienyloxycarbonyl, $C_{1-4}$ alkylsulfonyl which may be substituted with halogen, a $C_{1-4}$ acyl group which may be substituted with halogen; and (b) an agrochemically acceptable carrier.

2. A tetrahydropyrimidine compound of the formula

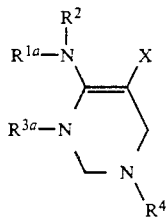

wherein $R^{1a}$, $R^2$, $R^{3a}$ and $R^4$ are the same or different and are each independently selected from the group consisting of:

a hydrogen atom;

a hydrocarbon group selected from the group consisting of an alkyl group of 1 to 15 carbon atoms, a cycloalkyl group of 3 to 10 carbon atoms, an alkenyl group of 2 to 10 carbon atoms, an alkynyl group of 2 to 20 carbon atoms, a cycloalkenyl group of 3 to 10 carbon atoms, an aryl group of 6 to 10 carbon atoms, and an aralkyl group of 7 to 10 carbon atoms, said hydrocarbon group being unsubstituted or substituted with 1 to 5 substituents selected from the group consisting of nitro, hydroxyl, oxo, thioxo, cyano, carbamoyl, carboxyl, $C_{1-4}$ alkoxycarbonyl, sulfo, halogen, $C_{1-4}$ alkoxy, phenoxy, $C_{1-4}$ alkylthio, phenylthio, $C_{1-4}$ alkylsulfinyl, $C_{1-4}$ alkylsulfonyl, amino, $C_{2-6}$ acylamino, methylamino, ethylamino, n-propylamino, isopropylamino, n-butylamino, dimethylamino, diethylamino, cyclohexylamino, anilino, $C_{2-4}$ acyl, benzoyl and a heterocyclic group selected from the group consisting of 2-thienyl, 3-thienyl, 2-furyl, 3-furyl, 3-pyrazolyl, 4-pyrazolyl, 5-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isooxazolyl, 4-isooxazolyl, 5-isooxazolyl, 2-imidazolyl, 4-imidazolyl, 5-imidazolyl, 1,2,3-triazolyl, 1,2,4-triazolyl, 1H-tetrazolyl, 2H-tetrazolyl, 2-pyridyl, 3-pyridyl, 4-pyridyl, 2-pyrimidyl, 4-pyrimidyl, 5-pyrimidyl, 3-pyridazinyl, 4-pyridazinyl, quinolyl, isoquinolyl and indolyl, said heterocyclic group being unsubstituted or substituted with 1 to 4 substituents selected from the group consisting of a halogen atom, $C_{1-4}$ alkyl, halophenoxy, and halo $C_{1-4}$ alkyl, and when said hydrocarbon group is aryl, aralkyl, cycloalkyl or cycloalkenyl, said substituents further including a member selected from the group consisting of an alkyl group of 1 to 15 carbon atoms, an alkenyl group of 2 to 10 carbon atoms, an alkynyl group of 2 to 20 carbon atoms and an aryl group of 6 to 10 carbon atoms; and a five- to eight-membered heterocyclic ring or a fused ring derivative thereof selected from the group consisting of 2-thienyl, 3-thienyl, 2-furyl, 3-furyl, 2-pyrrolyl, 3-pyrrolyl, 2-pyridyl, 3-pyridyl, 4-pyridyl, 2-oxazolyl, 4-oxazolyl, 5-oxazolyl, 2-thiazolyl, 4-thiazolyl, 5-thiazolyl, 3-pyrazolyl, 4-pyrazolyl, 5-pyrazolyl, 2-imidazolyl, 4-imidazolyl, 5-imidazolyl, 3-isooxazolyl, 4-isooxazolyl, 5-isooxazolyl, 3-isothiazolyl, 4-isothiazolyl, 5-isothiazolyl, 3-(1,2,4-oxadiazolyl), 5-(1,2,4-oxadiazolyl), 1,3,4-oxadiazolyl, 3-(1,2,4-thiadiazolyl), 5-(1,2,4-thiadiazolyl), 1,3,4-thiadiazolyl, 4-(1,2,3-thiadiazolyl), 5-(1,2,3-thiadiazolyl), 1,2,5-thiadiazolyl, 1,2,3-triazolyl, 1,2,4-triazolyl, 1H-tetrazolyl, 2H-tetrazolyl, N-oxido-2,3-pyridyl, N-oxido-4-pyridyl, 2-pyrimidyl, 4-pyrimidyl, 5-pyrimidyl, N-oxido-2-pyrimidyl, N-oxido-4-pyrimidyl, N-oxido-5-pyrimidyl, 3-pyridazinyl, 4-pyridazinyl, pyrazinyl, N-oxido-3-pyridazinyl, N-oxido-4-pyridazinyl, benzofuryl, benzothiazolyl, benzoxazolyl, triazinyl, oxotriazinyl, tetrazolo(1,5-b)pyridazinyl, triazolo(4,5-b)pyridazinyl, oxoimidazinyl, dioxotriazinyl, pyrrolidinyl, piperidinyl, pyranyl, thiopyranyl, 1,4-oxazinyl, morpholinyl, 1,4-thiazinyl, 1,3-thiazinyl, piperazinyl, benzimidazolyl, quinolyl, isoquinolyl, cinnolinyl, phthalazinyl, quinazolinyl, quinoxalinyl, indolidinyl, quinolidinyl, 1,8-naphthyridinyl, purinyl, pteridinyl, dibenzofuranyl, carbazolyl, acridinyl, phenanthridinyl, phenazinyl, phenothiazinyl and phenoxazinyl, said heterocyclic ring or fused ring derivative thereof being unsubstituted or substituted with 1 to 5 substituents selected from the group consisting of said substituents for said hydrocarbon group;

wherein said at least one of $R^{1a}$ and $R^{3a}$ is a group of the formula $-(CH_2)_n-R^5$ (where $R^5$ is selected from the group consisting of said unsubstituted five- to eight-membered heterocyclic ring, said substituted five- to eight-membered heterocyclic ring, said fused ring derivative thereof and an aryl group of 6 to 10 carbon atoms substituted with 1 to 3 halogen atoms, and n is equal to 0 or 1); and X represents an electron accepting group selected from the group consisting of cyano, nitro, $C_{1-4}$ alkoxycarbonyl, hydroxycarbonyl, $C_{6-10}$ aryloxycarbonyl, pyridyloxycarbonyl, thienyloxycarbonyl, $C_{1-4}$ alkylsulfonyl which may be substituted with halogen and a $C_{1-4}$ acyl group which may be substituted with halogen; or a salt thereof.

3. The tetrahydropyrimidine compound or salt according to claim 2 wherein $R^5$ represents a halopyridyl group or a halothiazolyl group.

4. A tetrahydropyrimidine compound according to claim 2 represented by the formula

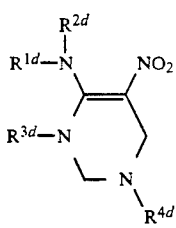

wherein one of $R^{1d}$ and $R^{3d}$ is $R^{5b}$—$CH_2$— (wherein $R^{5b}$ is a halopyridyl or halothiazolyl group) and the other is H or a $C_1$-$C_3$ alkyl group, $R^{2d}$ is H or a $C_1$-$C_3$ alkyl group and is a $C_{7-10}$ aralkyl group.

5. A compound according to claim 4, wherein $R^{1d}$ is 6 bromo or chloro-3-pyridylmethyl, 2 chloro-5-thiazolylmethyl or a $C_{1-3}$ alkyl group.

6. A compound according to claim 4, wherein $R^{3d}$ is 6-bromo or chloro-3-pyridylmethyl group.

7. A compound according to claim 4, wherein $R^{1d}$ is 3-pyridylmethyl group.

8. A compound according to claim 4, wherein $R^{1d}$ is methyl group.

9. A compound according to claim 4, wherein $R^{2d}$ is H.

10. A compound according to claim 4, wherein $R^{4d}$ is a C7-10 aralkyl group.

11. A compound according to claim 4, wherein $R^{3d}$ or $R^{4d}$ is methyl group.

12. A compound according to claim 4, wherein $R^{4d}$ is benzyl group.

13. A compound according to claim 4, which is 1-benzyl-3-(6-chloro-3-pyridylmethyl)-4-methylamino-5-nitro-1,2,3,6-tetrahydropyrimidine.

14. A compound according to claim 4, which is 1,3-dimethyl-4-(2-chloro-5-thiazolylmethyl)amino-5-nitro-1,2,3,6-tetrahydropyrimidine.

15. An insect control composition comprising an insecticidally effective amount of a compound or salt thereof as defined in claim 2 and an agrochemically acceptable carrier.

16. An insect control composition comprising an insecticidally effective amount of a compound or salt thereof as defined in claim 4 and an agrochemically acceptable carrier.

17. A method of combatting insects wherein there is used as an insecticidal agent a composition of claim 15.

* * * * *